United States Patent
Yi et al.

(10) Patent No.: US 7,972,865 B2
(45) Date of Patent: Jul. 5, 2011

(54) SENSOR FOR DETECTING AND DIFFERENTIATING CHEMICAL ANALYTES

(75) Inventors: Dechang Yi, Metuchen, NJ (US); Lawrence R. Senesac, Knoxville, TN (US); Thomas G. Thundat, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 60 days.

(21) Appl. No.: 12/198,580

(22) Filed: Aug. 26, 2008

(65) Prior Publication Data

US 2010/0055801 A1    Mar. 4, 2010

(51) Int. Cl.
*G01N 27/04* (2006.01)
*G01N 33/22* (2006.01)

(52) U.S. Cl. ..... 436/149; 73/35.02; 73/35.05; 73/35.14; 73/35.16; 73/23.2; 73/31.01; 73/31.05; 73/31.03; 310/306; 310/307; 422/90; 422/91; 422/94; 422/95; 422/88

(58) Field of Classification Search .............. 422/90, 422/91, 94, 95, 88; 73/35.02, 35.05, 35.14, 73/35.16, 23.2, 31.01, 31.05, 31.03; 310/306, 310/307; 436/149
See application file for complete search history.

(56) References Cited

U.S. PATENT DOCUMENTS

| | | | | |
|---|---|---|---|---|
| 4,094,608 A * | 6/1978 | Young | ............ | 356/326 |
| 4,703,555 A | 11/1987 | Hübner | | |
| 4,942,299 A * | 7/1990 | Kazmerski | ............ | 850/9 |
| 5,161,147 A * | 11/1992 | Goldberg et al. | ............ | 369/100 |
| 5,445,008 A * | 8/1995 | Wachter et al. | ............ | 73/24.06 |
| 5,464,977 A * | 11/1995 | Nakagiri et al. | ............ | 250/234 |
| 5,522,980 A * | 6/1996 | Hobbs et al. | ............ | 204/432 |
| 5,719,324 A * | 2/1998 | Thundat et al. | ............ | 73/24.01 |
| 5,770,856 A * | 6/1998 | Fillard et al. | ............ | 250/234 |
| 5,918,263 A * | 6/1999 | Thundat | ............ | 73/35.16 |
| 5,977,544 A * | 11/1999 | Datskos et al. | ............ | 250/338.1 |
| 6,207,938 B1 * | 3/2001 | Taylor et al. | ............ | 219/505 |
| 6,212,939 B1 * | 4/2001 | Thundat | ............ | 73/24.02 |
| 7,508,294 B2 * | 3/2009 | Cabal et al. | ............ | 337/36 |
| 2004/0099047 A1 | 5/2004 | Raisanen | | |
| 2005/0025215 A1 | 2/2005 | Arndt et al. | | |
| 2006/0032289 A1 * | 2/2006 | Pinnaduwage et al. | ...... | 73/25.05 |
| 2008/0116490 A1 | 5/2008 | Stewart et al. | | |

OTHER PUBLICATIONS

Bunte, G.; Hürttlen, J.; Pontius, H.; Hartlieb, K.; Krause, H. "Gas Phase Detection of Explosives Such as 2,4,6-Trinitrotoluene by Molecularly Imprinted Polymers," *Analytica Chima Acta*, 2007 591(1), pp. 49-56.

(Continued)

*Primary Examiner* — Vickie Kim
*Assistant Examiner* — Rebecca Fritchman
(74) *Attorney, Agent, or Firm* — Brinks Hofer Gilson & Lione (57) ABSTRACT

A sensor for detecting and differentiating chemical analytes includes a microscale body having a first end and a second end and a surface between the ends for adsorbing a chemical analyte. The surface includes at least one conductive heating track for heating the chemical analyte and also a conductive response track, which is electrically isolated from the heating track, for producing a thermal response signal from the chemical analyte. The heating track is electrically connected with a voltage source and the response track is electrically connected with a signal recorder. The microscale body is restrained at the first end and the second end and is substantially isolated from its surroundings therebetween, thus having a bridge configuration.

20 Claims, 7 Drawing Sheets

OTHER PUBLICATIONS

Colton, R.J.; Russell, J.N. "Perspectives—Counterterrorism—Making the World a Safer Place," *Science*, 2003, 299, pp. 1324-1325.

Dutta, P.; Senesac, L.R.; Lavrik, N. V.; Datskos, P.G.; Sepaniak, M.J. "Response Signatures for Nanostructured, Optically-Probed, Functionalized Microcantilever Sensing Arrays," *Sensor Letters*, 2004, 2, p. 1-8.

Fainberg, A. "Explosives Detection for Aviation Security," *Science*, 1992, 255(5051), pp. 1531-1537.

Hallowell, S.F. "Screening People for Illicit Substances: A Survey of Current Portal Technology," *Talanta*, 2001, 54, pp. 447-458.

Hill, H.H.; Simpson, G. "Capabilities and Limitations of Ion Mobility Spectrometry for Field Screening Applications," *Field Anal. Chem. and Tech.*, 1997, 1(3), pp. 119-134.

Houser, E.J.; Mlsna, T.E.; Nguyen, V.K.; Chung, R.; Mowery, R.L.; McGill, R.A. "Rational Materials Design of Sorbent coatings for Explosives: Applications with Chemical Sensors," *Talanta*, 2001 54, pp. 469-485.

Hsieh, M.D.; Zellers, E.T. "Limits of Recognition for Simple Vapor Mixtures Determined with a Microsensor Array," *Anal. Chem.*, 2004, 76, pp. 1885-1895.

Lee, J.; Beechem, T.; Wright, T.L.; Nelson, B.A.; Graham, S.; King, W.P. "Electrical, Thermal, and Mechanical Characterization of Silicon Microcantilever Heaters," *JMEMS.*, 2006, 15(6), p. 1644-1655.

Lu, C.J.; Whiting, J.; Sacks, R.D.; Zellers, E.T. "Portable Gas Chromatograph with Tunable Retention and Sensor Array Detection for Determination of Complex Vapor Mixtures," *Anal. Chem.*, 2003, 75(6), pp. 1400-1409.

Masel, R.I. *Principles of Adsorption and Reaction on Solid Surfaces*, John Wiley & Sons, New York, USA, 1996, p. 509-514.

Mu, R.; Ueda, A.; Wu, M.H.; Tung, Y.S.; Henderson, D.O.; Chamberlain, R.T.; Curby, W.; Mercado, A. "Experimental and Theoretical Demonstration of the Interfacial Interaction Potential Between an Adsorbed Film and a Smooth Substrate," *J. Phys. Chem. B, 2000*, 104, pp. 105-109.

Ostafin, M.; Nogaj, B. "Detection of Plastic Explosives in Luggage with $^{14}N$ Nuclear Quadrupole Resonance Spectroscopy," *Applied Magnetic Resonance*, 2000, 19, pp. 571-578.

Pinnaduwage, L.A.; Gehl, A.; Hedden, D.L.; Muralidharan, G.; Thundat, T.; Lareau, R.T.; Sulchek, T.; Manning, L.; Rogers, B.; Jones, M.; Adams, J.D. "A Microsensor for Trinitrotoluene Vapour," *Nature*, 2003, 425, p. 474.

Pinnaduwage, L.A.; Boiadjiev, V.; Hawk, J.E.; Thundat, T. "Sensitive Detection of Plastic Explosives with Self-Assembled Monolayer-Coated Microcantilevers," *Appl. Phys. Lett.*, 2003, 83(7), pp. 1471-1473.

Pinnaduwage, L.A.; Wig, A.; Hedden, D.L.; Gehl, A.; Yi, D.; Thundat, T.; Lareau, R.T. "Detection of Trinitrotoluene Via Deflagration on a Microcantilever," *J. Appl. Phys.*, 2004, 95(10), pp. 5871-5875.

Pinnaduwage, L.A.; Yi, D.; Tian, F.; Thundat, T.; Lareau, R.T. "Adsorption of Trinitrotoluene on Uncoated Silicon Microcantilever Surfaces," *Langmuir*, 2004, 20, pp. 2690-2694.

Senesac, L.R.; Dutta, P.; Datskos, P.G.; Sepaniak, M.J. "Analyte Species and Concentration Identification Using Differentially Functionalized Microcantilever Arrays and Artificial Neural Networks," *Anal. Chim. Acta*, 2006, 558, pp. 94-101.

Sharma, S.K.; Misra, A.K.; Sharma, B. "Portable Remote Raman System for Monitoring Hydrocarbon, Gas Hydrates and Explosives in the Environment," *Spectrochimica Acta Part A*, 2005, 61, pp. 2404-2412.

Walt, D.R. "Electronic Noses: Wake Up and Smell the Coffee," *Anal. Chem.*, 2005, p. 45A.

Yinon, J., Ed. "Chapter 5—Explosive Vapor Detection Using Microcantilever Sensors," *Counterterrorist Detection Techniques of Explosives*, Elsevier B.V., 2007, pp. 109-130.

Yinon, J. "Detection of Explosives by Electronic Noses," *Anal. Chem.*, 2003, pp. 99A-105A.

The International Search Report and the Written Opinion of the International Searching Authority dated Dec. 15, 2009 for International Patent Application No. PCT/US2009/054318.

\* cited by examiner

SENSOR FOR DETECTING AND DIFFERENTIATING CHEMICAL ANALYTES

FEDERALLY SPONSORED RESEARCH OR DEVELOPMENT

This invention was made with government support under Contract. No. DE-AC05-00OR22725 awarded by the U.S. Department of Energy. The government has certain rights in this invention.

TECHNICAL FIELD

The present disclosure is related generally to sensing devices and more particularly to microscale sensors for detecting chemical analytes.

BACKGROUND

Despite its immediate relevance in homeland security applications, high sensitivity detection of explosives using real-time, miniature sensors still remains as a crucial challenge. Although widely used and highly effective, trace explosive detection based on canines is neither cost effective nor suitable for mass deployment. Currently available technologies, such as ion mobility spectrometry and nuclear quadrupole resonance spectroscopy, are bulky and expensive. Optical spectroscopic techniques, such as Raman and laser-induced breakdown spectroscopies, are highly selective but suffer from poor sensitivity. Micro-electro-mechanical systems (MEMS) can potentially satisfy many of the requirements for an ideal compact chemical sensor, such as low-power consumption, real-time operation, and high sensitivity. However, the suitability of MEMS as practical sensors for vapor detection has traditionally been limited by a lack of chemical selectivity.

The selectivity challenge encountered with micromechanical sensors is not unique to MEMS. Other gravimetric sensors such as quartz crystal microbalance (QCM) and surface acoustic wave (SAW) devices, also lack intrinsic selectivity and rely on selective interfaces for chemical speciation. The need for chemical selectivity forces the use of separation techniques or the use of highly selective recognition layers that are irreversible at room temperature. Although attractive from an analytical standpoint, incorporation of separation techniques with MEMS sensors poses integration problems, especially for explosives detection due to the large volumes of air needed for sample collection.

At present there exist no room-temperature reversible receptors that are highly selective for vapor molecules, especially explosive vapors. Designing high specificity molecular recognition layers for small molecules is challenging due to the limited number of chemical interactions that can serve as a basis for designing selective layers while satisfying the highly desirable sensor attribute of room temperature reversibility.

Approaches for achieving selectivity by using sensor arrays modified with partially selective interfaces and pattern recognition work are presently underway. The molecular recognition interfaces based on weak interactions are not specific enough to produce unique responses with a single sensor. Unique responses (orthogonal) cannot be obtained if the mechanism behind individual sensor elements is unspecific, for example, hydrogen bonding of analyte with the chemoselective layer. Increasing the number of sensor elements in the array for pattern recognition analysis can improve the selectivity only if the responses from individual sensing elements are orthogonal. However, there are only a limited number of weak reversible chemical interactions that can serve as a basis for designing the selective layers. Therefore, despite the chemical sensing advantages offered by microfabricated sensors, their use as a practical sensor may be limited without the development of techniques that can generate orthogonal responses.

BRIEF SUMMARY

A sensor and method that can provide unique thermal response data for the detection and differentiation of explosives and other chemical analytes are described.

The sensor includes a microscale body having a first end and a second end and a surface between the ends for adsorbing a chemical analyte. The surface includes at least one conductive heating track for heating the chemical analyte and also a conductive response track, which is electrically isolated from the heating track, for producing a thermal response signal from the chemical analyte. The heating track is electrically connected with a voltage source and the response track is electrically connected with a signal recorder. The microscale body is restrained at the first end and the second end and is substantially isolated from its surroundings therebetween, thus having a bridge configuration.

The method includes providing a microscale body having a first end and a second end and a surface between the ends, where the surface includes at least one conductive heating track and a conductive response track, which is electrically isolated from the heating track. The microscale body is restrained at the first end and the second end and is substantially isolated from its surroundings between the ends, thus having a bridge configuration. The method includes adsorbing a chemical analyte onto the surface of the microscale body and applying an increasing voltage to the heating track to heat the microscale body for a time duration sufficient to remove substantially all of the chemical analyte from the surface. A resistance of the response track is measured during the application of the increasing voltage over at least a portion of the time duration of the heating to generate a plurality of thermal response signals. The thermal response signals are recorded to obtain a first thermal response profile.

DETAILED DESCRIPTION

A novel microbridge sensor that generates a unique thermal response from an adsorbed chemical analyte to achieve chemical selectivity without sacrificing sensitivity or reversibility is described. Due to its micro- and sub-microscale dimensions, the microbridge sensor may be heated to more than 500 degrees in 50 milliseconds by passing current through one or more heating tracks embedded in its surface. A measuring track changes resistance with temperature to provide a thermal response signal. The thermal response spectrum or profile over the duration of the heating provides a signature of the adsorbed analyte. The microbridge sensor is capable of differentiating explosive from non-explosive materials, and is further capable of differentiating individual explosive molecules such as trinitrotoluene (TNT), pentaerythritol tetranitrate (PETN), and cyclotrimethylenetrinitramine (RDX). The microbridge sensor may also be applied to the detection of other chemical analytes.

Figure 1A:
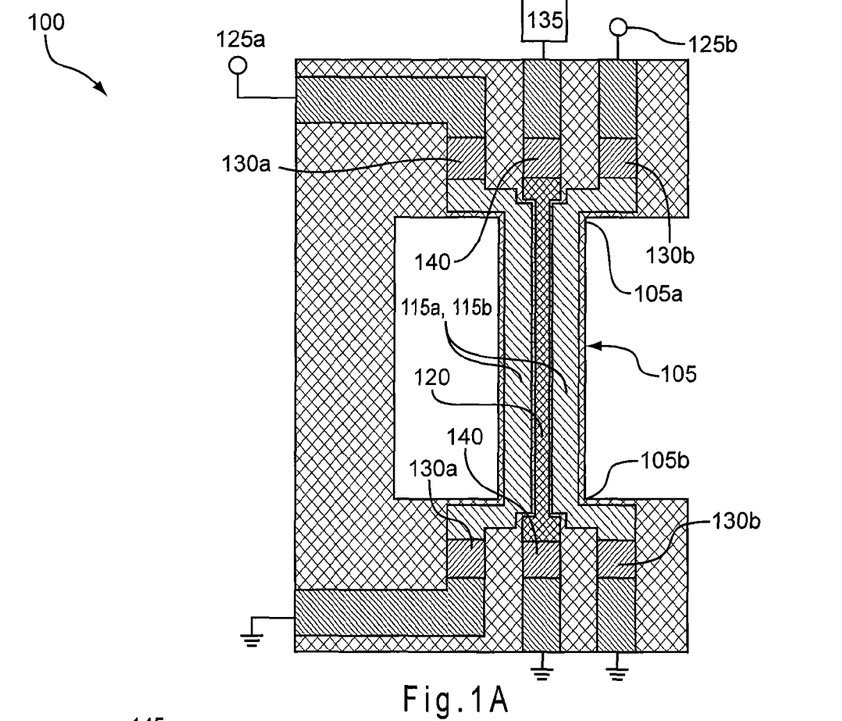
FIG. 1A is a schematic of one embodiment of the microbridge sensor.

Referring to FIG. 1A, the sensor 100 includes a microscale body 105 having a first end 105a and a second end 105b and a surface 110 between the ends 105a, 105b. Having a bridge configuration, the microscale body 105 is restrained at the first end 105a and the second end 105b and is substantially isolated from its surroundings between the two ends 105a, 105b.

The microscale body (or microbridge) 105 includes at least one conductive heating track 115a for heating molecules adsorbed onto the surface 110 and a conductive response track for producing a thermal response signal from the adsorbed molecules. The conductive heating track 115a preferably extends from the first end 105a to the second end 105b of the microbridge 105 and is electrically connected to a voltage source 125a. The conductive response track 120 is electrically isolated from the heating track 115a and is electrically connected with a signal recorder 135. Preferably, the conductive response track 120 extends from the first end 105a to the second end 105b of the microbridge 105. According to the embodiment shown in FIG. 1A, the microscale body 105 includes two conductive heating tracks 115a, 115b disposed on either side of the conductive response track 120. When the microscale body 105 and any adsorbed analyte molecules are heated by passing electrical current through the conductive heating tracks 115a, 115b, the resistance of the conductive response track 120 varies sensitively as a function of temperature. Each heating track 115a, 115b is joined to electrical contacts 130a, 130b connected to the voltage source 125a, 125b and ground. The response track 120 is joined to electrical contacts 140, which are connected to a signal recorder 135 and ground.

Figure 1B:
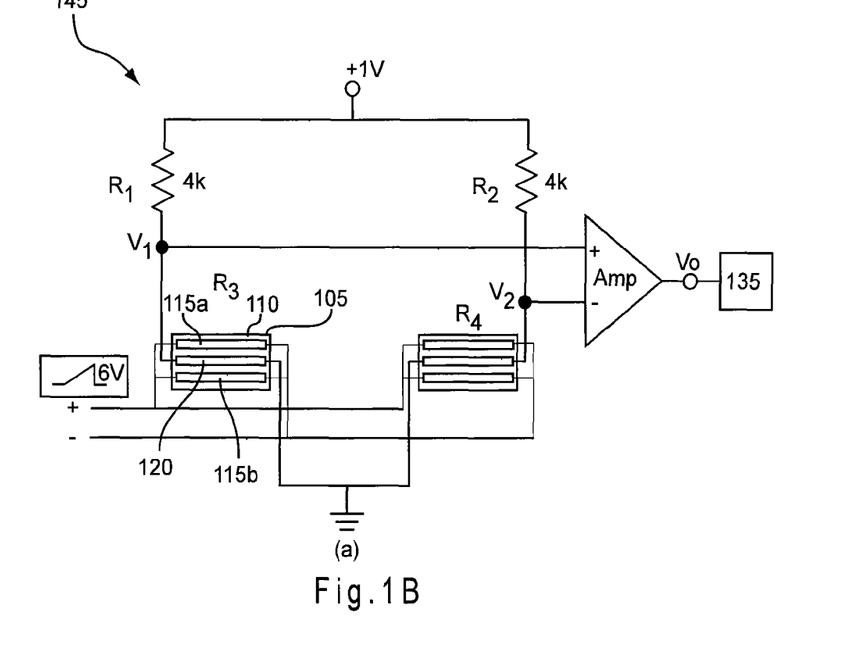
FIG. 1B shows the microbridge sensor of FIG. 1A as part of a Wheatstone bridge circuit.

The microbridge sensor 100 is shown as part of a Wheatstone bridge circuit 145 in FIG. 1B. The Wheatstone bridge circuit 145 is employed to measure small changes in the resistance of the conductive response track 120. The output of the Wheatstone bridge circuit 145 is transmitted to the signal recorder 135. The circuit 145 includes two fixed resistors $R_1$ and $R_2$ and two variable resistors, $R_3$ and $R_4$. The fixed resistors $R_1$ and $R_2$ are identical resistors with constant resistance. Variable resistor $R_3$ is used for sensing and its resistance varies during the measurement. Variable resistor $R_4$ is used to balance $R_3$ before the measurement. The response track 120 of the analyte-loaded microscale body 105 serves as variable resistor $R_3$ and the response track of an unloaded but otherwise identical microbridge serves as variable resistor $R_4$. The configuration allows a differential measurement of the resistance of the sensor to be made by comparing the resistance of the analyte-loaded microscale body 105 to the resistance of the unloaded microbridge, which is not exposed to the analyte vapor.

If the Wheatstone bridge circuit 145 is balanced, namely if $R_1=R_2$ and $R_3=R_4$, then the output of the circuit, namely $V_1-V_2$, is zero. During the measurement, the resistance of $R_3$ varies, and thus $V_1$ varies. Since $R_2$ and $R_4$ are fixed in the measurement, $V_2$ does not vary, and thus the output of the bridge circuit, namely $V_1-V_2$, is related only to the change of $R_3$. Generally, an amplifier is connected with the bridge circuit to increase the gain. By using the Wheatstone bridge circuit 145, the resistance change of $R_3$ can be determined from the voltage output $V_O$.

It is possible to heat the microscale body to hundreds of degrees centigrade in milliseconds due to the body's extremely low thermal mass. Rapid and controllable heating rates, dT/dt, where T is the temperature and t is the time, of up to $10^{8°}$ C./s can be achieved with the sensor configurations described and depicted herein. The heating rate may be in the range of from about $10^{3°}$ C./s to $10^{5°}$ C./s, and a heating rate of about $10^{4°}$ C./s has been found to be particularly advantageous for obtaining detailed thermal response profiles.

To achieve the desired heating rates, an appropriate voltage is applied to the heating track over a short time period. Generally, given the heat capacity and the track resistance of embodiments of the microbridge sensor described and depicted herein, an increasing voltage of up to 10 V is appropriate. For example, a voltage that increases to a value in the range of from 5 V to 8 V may be applied to the heating track(s). The voltage may be ramped up or pulsed over a time duration of at least about 10 ms and typically no more than about 100 ms. The time duration of the heating may be, for example, from about 30 ms to about 70 ms. It may be advantageous to apply a linearly increasing voltage to the heating track for a time duration in this range. Alternatively, the voltage may be applied as a step function (pulsed) for a shorter time duration (e.g., about 10 ms). The voltage may also be applied at different rates $(dV_x/dt_x)$ over the time duration of the heating. For example, a voltage may initially be applied to the heating track at a first rate $dV_1/dt_1$ and then applied to the track at a second rate $dV_2/dt_2$ for a remainder of the time duration of the heating.

The tunable heating rate dT/dt makes it possible to achieve chemical speciation for sub-nanogram quantities of material without relying on receptors or separation methods. Unlike the deflagration of adsorbed explosives on cantilevers, which fails to achieve speciation, the controlled heating of chemical analytes on microbridge sensors provides very high chemical selectivity.

The low thermal mass of the microbridge, which facilitates the rapid heating of the chemical analyte, can be attributed to its extremely small dimensions (e.g., submicroscale thickness). Presently fabricated sensors include a thin rectangular microscale body, and thickness is a key parameter in determining the sensitivity of the device. The detection sensitivity depends on how effectively heat released from or absorbed by the deposited analyte can raise or lower the temperature of the microscale body. A thinner device has less heat capacity, and thus it can be heated or cooled with a smaller amount of adsorbed material. On the other hand, the thickness of the sensor is preferably large enough to impart structural stability to the device. For example, the microscale body is preferably at least about 10 nm (0.01 micron) in thickness, and may advantageously be at least about 50 nm in thickness. It is also preferred that the thickness of the microscale body is no more than about 700 nm. It may be particularly advantageous for the thickness of the microscale body to be about 500 nm or less, about 300 nm or less, or about 100 nm or less. For example, the thickness of the microscale body of the sensor may range from about 10 nm to about 700 nm, from about 50 nm to about 500 nm, or from about 100 nm to about 300 nm.

It is also desirable that the area of the surface of the microbridge onto which the analyte is adsorbed is optimized. If the surface area (in particular, the length) of the sensor is too small, the heating of the bridge may be diminished due to end effects, with the restrained ends of the sensor acting as relatively massive heat sinks. In addition, the amount of analyte that may be adsorbed onto the sensor decreases as the area of the adsorbing surface is reduced. For example, if the length of the sensor is halved compared to the original length, the surface area available to adsorb the chemical analyte is correspondingly reduced. Hence, despite the reduction in thermal mass gained by reducing the length, the sensitivity of the device may not increase since the amplitude of the response signal is related to the amount of the chemical analyte adsorbed onto the microscale body. On the other hand, a very large surface area that can adsorb a large amount of analyte may correspond to a microscale body that is too massive to heat at the desired rapid rates.

According to one embodiment, the surface of the device spans an area in the range of from about 0.01 $mm^2$ to about 0.1 $mm^2$. It may be particularly advantageous for the surface area of the device to be in the range of from about 0.03 $mm^2$ to about 0.07 $mm^2$. For example, the surface area may be about 0.05 $mm^2$.

Microbridges having a length of 300 microns, 400 microns, or 500 microns and a width of about 100 microns have been shown to work effectively. The length must be sufficient to effectively heat the bridge, as discussed above, and the width must be sufficient to allow the conductive tracks to be electrically insulated from each other by one or more regions of insulating material. Accordingly, the length of the microscale body from the first end to the second end may be in the range of from about 300 microns to about 500 microns, and the width of the microscale body may be in the range of from about 50 microns to about 150 microns, although other lengths and widths are also possible. A width in the range of from about 50 microns to about 100 microns may be advantageous, for example.

The sensitivity of the device may be enhanced by micromachining bridges having a decreased thermal mass in combination with a large surface area. It is contemplated that the microscale body may have configurations other than that shown in FIGS. 1 and 2 that provide a small thermal mass in conjunction with an optimized surface area. For example, the microscale body may have a cylindrical surface for adsorbing a chemical analyte. Other non-flat or non-smooth surface geometries (e.g., curved, roughened, corrugated, etc.) that allow the surface area to be maximized for a given microbody configuration are also possible.

To facilitate uniform heating of the surface of the sensor, the heating track(s) preferably cover substantially all of the surface except for the area occupied by the response track and the insulating regions. The heating track may have a width of from about 30 microns to about 40 microns and extend at least from the first end of the microscale body to the second end. The measuring track may have a width of from about 15 microns to about 25 microns and may also extend across the entire length of the microscale body. It is also contemplated that the heating and response tracks may have a curved, bent, or other non-straight or non-flat configuration.

Figure 2:
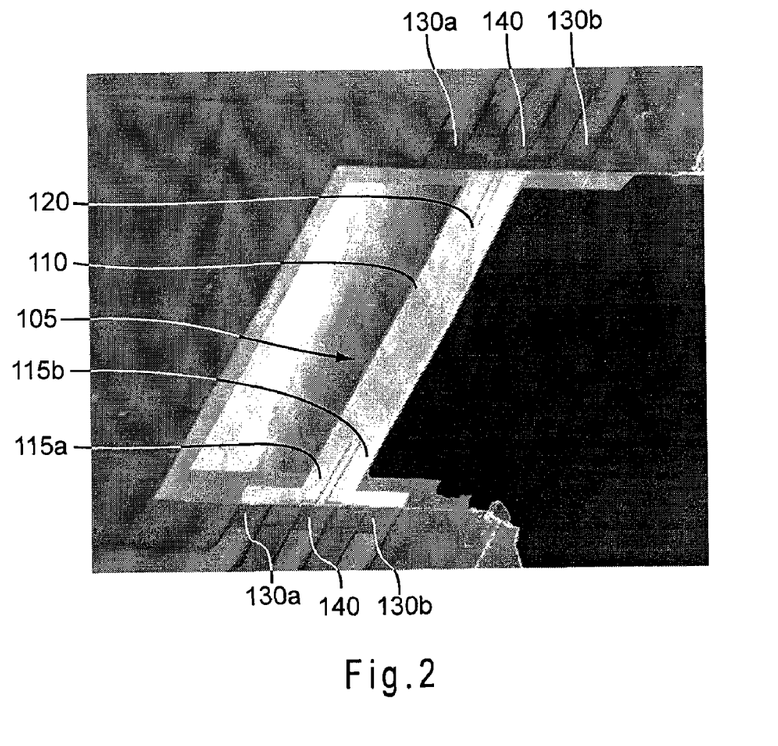
FIG. 2 is a scanning electron microscopy (SEM) image of the sensor shown in FIG. 1A.
Figure 3:
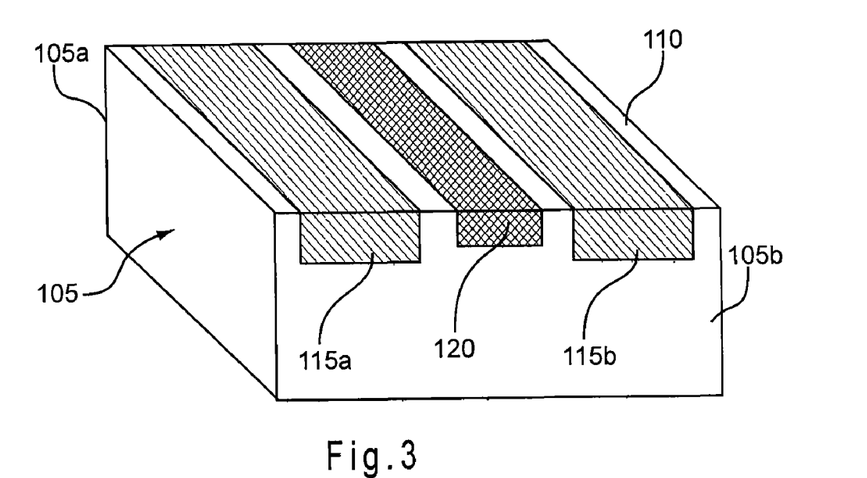
FIG. 3 is a cross-sectional view of a portion of the sensor.

The conductive heating and response tracks may be embedded into, deposited on, or otherwise included at or near the surface of the microscale body. For example, dopant atoms (e.g., boron) may be implanted into a silicon surface to form doped silicon of a suitable conductivity. The conductive tracks may then be defined by reactive ion etching, followed by deposition of silicon-rich nitride for insulation and then a polysilicon layer, as described in greater detail in the example below. FIG. 2 is a scanning electron microscope (SEM) image of an exemplary microbridge sensor fabricated from a silicon-on-insulator (SOI) wafer. The microbridge sensor is 450 microns in length, 100 microns in width, and 550 nm in thickness. Three electrically conducting tracks formed of doped silicon are buried in the wafer and separated from each other by thin layers of insulating silicon-rich nitride. The two outer tracks are the conductive heating tracks 115a, 115b and the inner track is the conductive response track 120, as shown schematically in FIG. 3.

A silicon body including conductive tracks formed of boron-doped silicon is described due to the ease of and/or availability of technology for fabricating the microbridge sensor from such materials. The sensor is not limited, however, to a body formed of silicon or to conductive tracks formed of doped silicon. The body may be formed of another material, such as a dielectric material, for example, and the conductive tracks could be formed of a metal or alloy deposited on or embedded into the dielectric material. There may be other suitable ways of forming (and materials from which to form) the body and conductive tracks of a microbridge sensor having a small thermal mass.

In an exemplary fabrication process, the microbridge sensor is constructed on a SOI wafer with a 400 nm buried oxide and a 340 nm device layer. In this example, the device layer is thinned to 200 nm by dry thermal oxidation, followed by boron doping to an active level of $7 \cdot 10^{19}$ $cm^{-3}$ using ion implantation. The conductive tracks are defined by reactive ion etching (RIE). A 250 nm layer of silicon-rich nitride is deposited by low pressure chemical vapor deposition (LPCVD) to provide electrical insulation between the tracks and to support the structure. A 90 nm layer of poly silicon is also deposited by LPCVD. The bridge and contact holes are defined using RIE and nitride etching (using phosphoric acid at 180° C.). The nitride on the back side of the wafer is patterned by RIE and the structures are released by a KOH etch at 80° C. During the release, the front side of the wafer is mechanically protected. Finally, a metal layer of Ti/Au is deposited and wires are defined by an etch sequence (KI, $I_2$ and HF). The microbridge fabricated in this exemplary process is 500 microns long and 100 microns wide. The two heating tracks are 35 microns in width and the measuring track in the center of the bridge is 10 microns wide. The heating tracks have a resistance of 1.77 k$\Omega$ and the measuring track has a resistance of 4.96 k$\Omega$. The doping level affects the resistance of the conductive tracks. A high doping level is selected to permit the bridge to be heated to a higher temperature before the intrinsic doping concentration interferes with the response signal.

The microbridge device may be kept in the open air directly in an explosive plume for evaluation or usage of the sensor. For evaluation purposes, the explosive plume may be produced by a custom-made vapor generator with a heated outlet, any example of which is described by Pinnaduwage et al. in *Langmuir* 2004, 20, 2690-2694. Explosive vapors created at elevated temperatures condense on the microbridge, which is maintained at room temperature. A voltage ramp is then used to increase the temperature of the microscale body at a desired high heating rate dT/dt. During heating, the adsorbed molecules melt, evaporate, decompose and/or desorb as a function of temperature, changing the resistance of the response track. For a dT/dt value of, for example, about $1.1 \times 10^{4\circ}$ C./s, the thermal response profile has a unique shape that depends on the adsorbed explosive.

The rate of heating depends on the mass of the bridge. Therefore, a bridge with added mass (adsorbed molecules) will have a different heating rate than an otherwise identical but unloaded bridge. Since all the adsorbed mass leaves (desorbs) from the loaded bridge by the end of the heating cycle, the thermal response obtained from a second heating step applied to the same bridge can serve as a baseline signal representing the bridge with no adsorbed mass.

Figure 4:
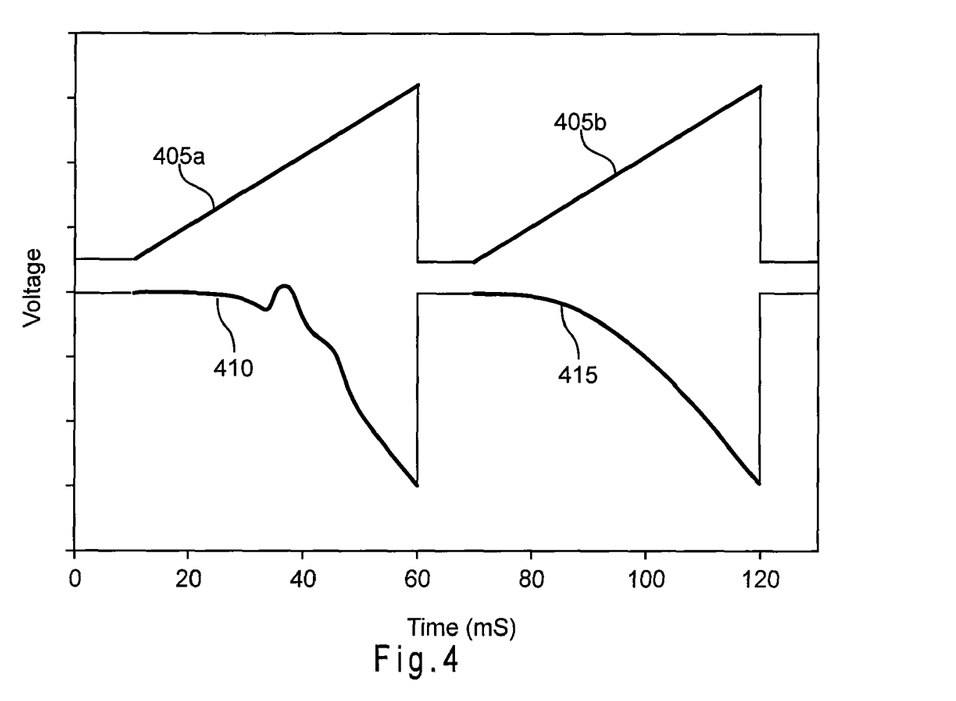
FIG. 4 is a plot showing two successive voltage ramps and the bridge response corresponding to each ramp; the first response corresponds to an analyte-loaded bridge and the second response corresponds to an identical but unloaded bridge.

FIG. 4 shows a linear voltage ramp of from 0 to 6.4 volts applied over a period of 50 milliseconds to the analyte-loaded bridge and then to the unloaded bridge. In this example, the analyte is PETN. A first voltage ramp 405*a* is applied to the PETN-loaded bridge to heat and ultimately desorb the PETN from the surface, producing a first thermal response profile 410, measured in terms of voltage. After the first heating cycle, the PETN is believed to be completely desorbed from the surface. A second thermal response profile 415 can then be obtained for the unloaded bridge during a second voltage ramp 405*b*.

Figure 5:
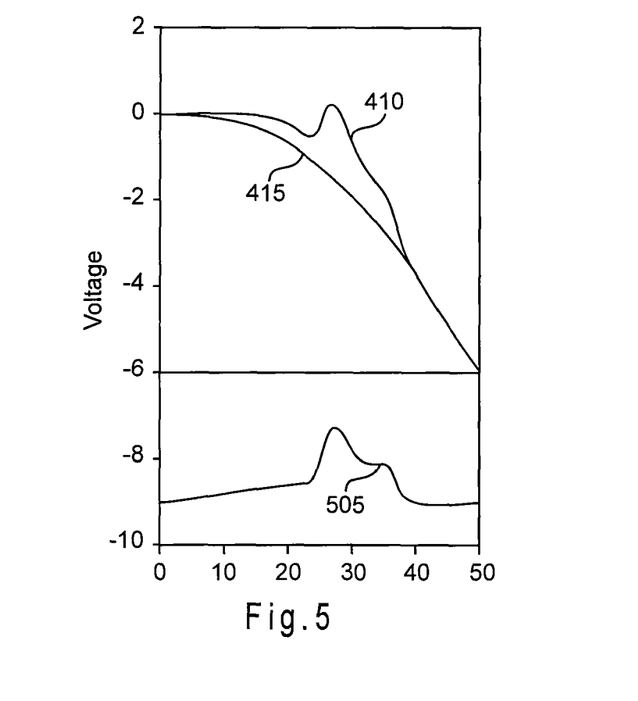
FIG. 5 shows a thermal response profile obtained by subtracting the second response of FIG. 4 (from the unloaded bridge) from the first response of FIG. 4 (from the analyte-loaded bridge)

Referring to FIG. 5, a thermal response profile 505 for the adsorbed chemical analyte in terms of voltage is created by subtracting the signal 410 of the PETN-loaded bridge from the signal 415 of the unloaded bridge.

The differential signal measured (see FIG. 5) as a function of heating time is proportional to the difference in resistance between the analyte-loaded bridge and the unloaded bridge, which is in turn proportional to the difference in their temperatures. A positive differential signal indicates that the temperature of the unloaded bridge is higher than that of the analyte-loaded bridge. The measurement is also proportional to the rate of change of thermal mass of the analyte-loaded bridge due to thermal desorption of the adsorbed molecules (dM/dt). The mass loss rate (dM/dt) is related to the product of dM/dT and the heating rate dT/dt. Since the observed signal is with respect to the same bridge, any mechanical buckling of the bridge under thermal stress does not play a role in the signal production. The thermal response profiles obtained from the differential measurements indicate how far the temperature of the loaded bridge lags behind that of the unloaded bridge. Explosives and other analytes may be distinguished using the shapes of their thermal response profiles.

Figure 6:
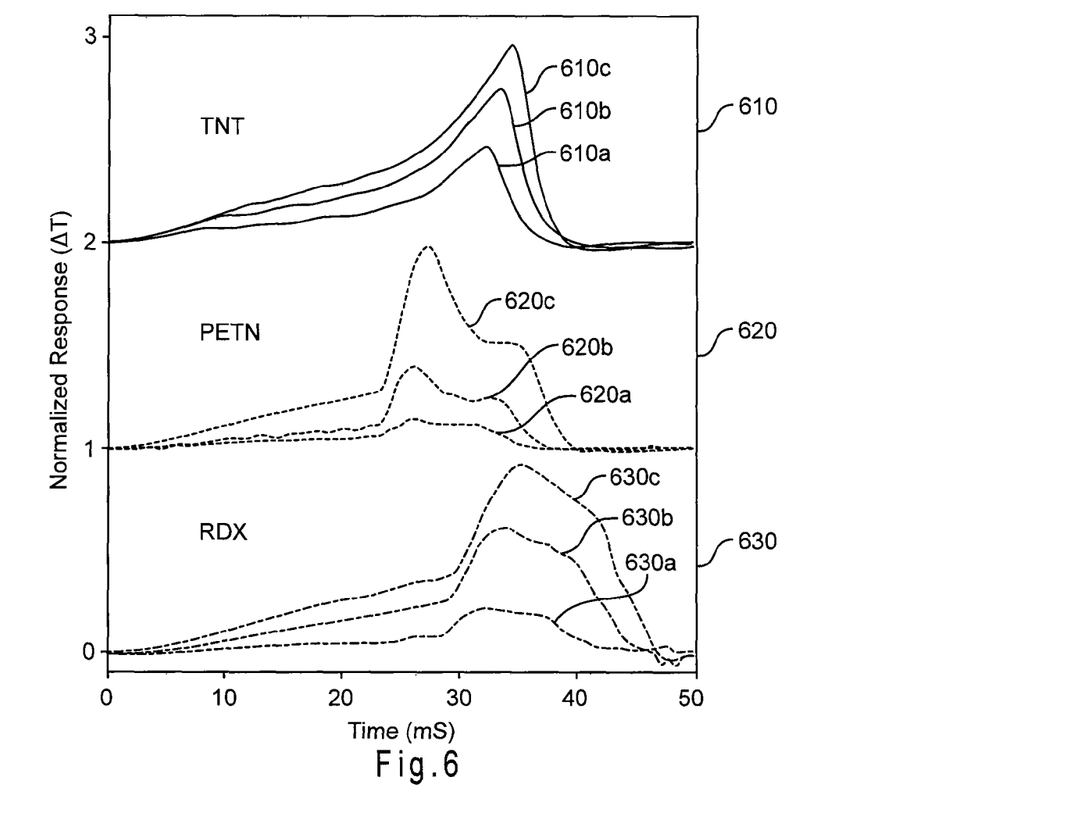
FIG. 6 shows thermal response profiles for three explosives heated in three separate experiments at different adsorbed mass levels.

Referring to FIG. 6, the three separate line curves plotted for each explosive correspond to three separate sensing experiments with varying amounts of explosive. The sensor output is plotted as a function of time (x-axis) due to the application of a linear heating voltage ramp (5.4 V in 50 milliseconds) with an average dT/dt of $10^{4\circ}$ C./s for each explosive. The explosives employed to obtain the curves 610, 620, 630 were TNT, PETN, and RDX, respectively. The three different curves (6X0*a*, 6X0*b*, and 6X0*c*; X=1, 2, or 3) shown for each explosive represent, respectively, 0.6, 1.2, and 2.4 nanograms of adsorbed explosive on the sensor. It can be seen that the amplitude of the response varies as a function of the mass of adsorbed explosive, but the shape of the response remains constant for a given explosive.

It is possible to obtain a thermal response from as little as a few picograms of adsorbate. A more sensitive device can obtain a signal from a smaller amount of adsorbate, but to obtain a detailed response profile during a voltage ramp, a larger amount of adsorbate may be advantageous. For example, 1 picogram to 6 picograms of adsorbate may be sufficient when a short (e.g., 10 ms) voltage pulse is applied to the microbridge, but 100 picograms to 600 picograms is preferred with a longer duration voltage ramp (e.g., over 50 ms). Generally, the amount of adsorbed chemical analyte is in the range of from about 1 picogram to about 1000 picograms (1 nanogram).

Figure 7:
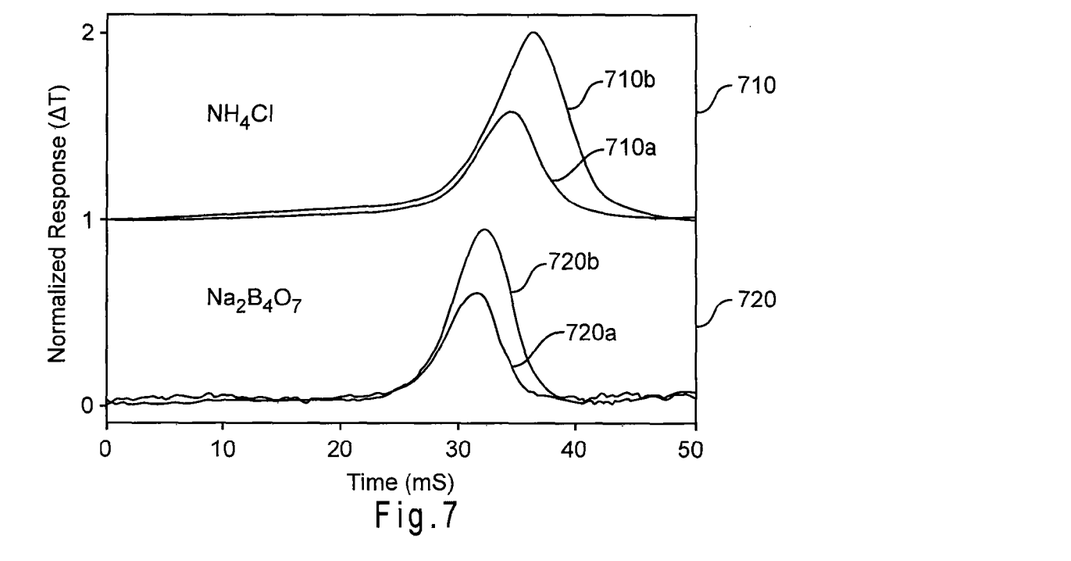
FIG. 7 shows thermal response profiles for two non-explosives heated in two separate experiments at different adsorbed mass levels.

FIG. 7 shows the thermal response of a bridge with adsorbed non-explosive molecules obtained with the same dT/dt as above. The non-explosive analytes employed to obtain the curves 710 and 720 were $NH_4Cl$ and $Na_2B_4O_7$, respectively. The response curves of the non-explosives appear as simple Gaussian peaks characteristic of evaporation events, where the peak positions vary with the specific material as well as the amount of material adsorbed. The two separate line curves (7X0*a* and 7X0*b*; X=1 or 2) plotted for each analyte correspond to two separate experiments with increasing mass of analyte, respectively. Unlike the thermal response profiles for explosives, the non-explosive profiles are featureless except for the Gaussian curvature.

Figure 8A:
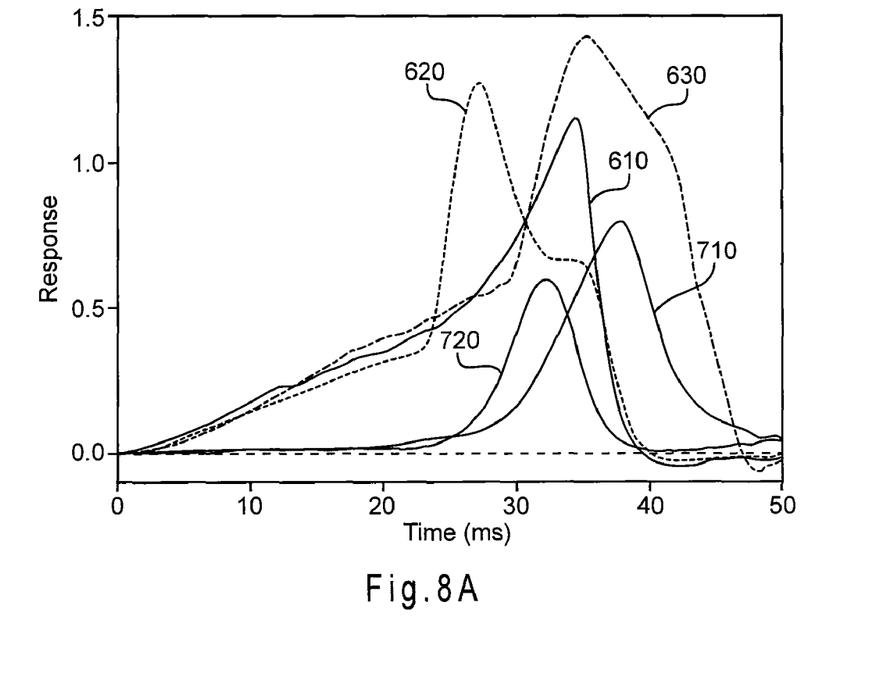
FIG. 8A shows thermal response profiles for the explosive and non-explosive analytes shown in FIGS. 6 and 7.
Figure 8B:
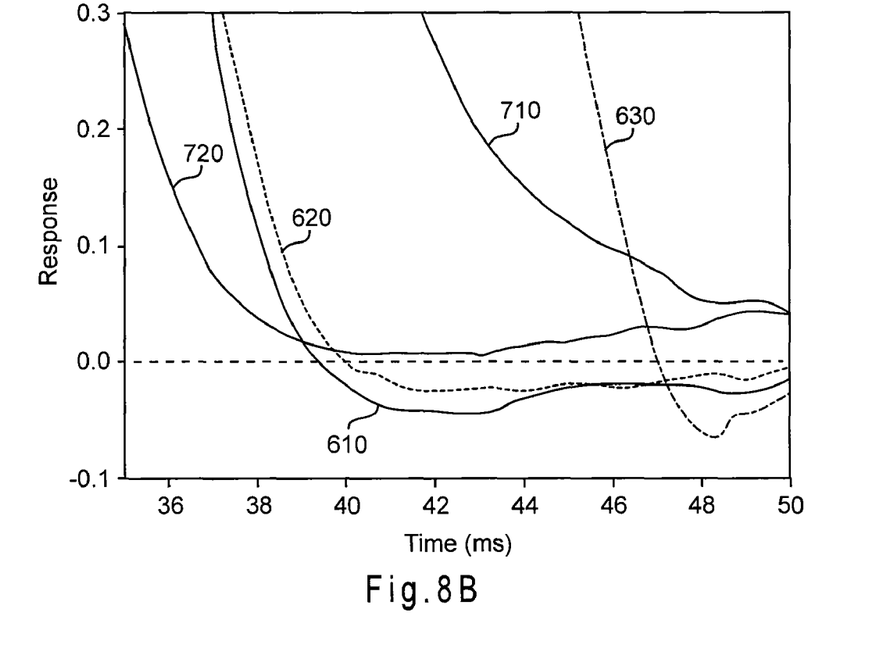
FIG. 8B is a close-up view of the lower right hand corner of the plot of FIG. 8A.

In FIG. 8A, the response curves of FIGS. 6 and 7 corresponding to the largest adsorbed mass for each analyte (TNT, PETN, RDX, $NH_4Cl$ and $Na_2B_4O_7$) are shown together for comparison. The response profiles for each explosive show distinct shapes due to a combination of melting, evaporation, and decomposition, while the response profiles for the non-explosive analytes have simple Gaussian shapes. Explosive responses tend to overshoot at the end of the response curve and dip to negative values, as shown in FIG. 8B, which is an enlarged view of the lower right hand corner of FIG. 8A. A signal below the dashed line indicates that the temperature of the bridge with adsorbed explosive is higher than the temperature of the bridge without the adsorbate present. This overshooting suggests that an exothermic decomposition of the adsorbed analyte has occurred. In contrast, the response profiles corresponding to the non-explosive analytes do not fall below the dashed line, which indicates that the temperature of the bridge with adsorbed non-explosive is always lower than the temperature of the bridge without the adsorbate present.

FIGS. 9A-9D are atomic force microscopy (AFM) images of adsorbed analyte on a silicon oxide surface. The AFM images show nucleation islands of adsorbed TNT (FIG. 9A), PETN (FIG. 9B), and RDX (FIG. 9C) on a silicon oxide surface of 10 square microns in area. The size of these islands increases with increasing exposure to the analyte.

Referring again to FIG. 8A, the response profile 610 for TNT shows a single peak with a slow rise and fast fall. The slow rise is consistent with melting and evaporation of nucleated TNT islands on the surface. Small islands evaporate faster than larger ones. AFM images of nucleated islands of TNT as a function of time at room temperature show residues left behind, probably crystalline TNT. It is believed that fast evaporation of islands leaves behind crystallites that exothermically decompose at higher temperature. The fast fall in the response curve is related to the rate at which the bridge's temperature is increasing, which may be attributed to a combination of exothermic decomposition and a decrease in thermal mass as material leaves the surface.

The shapes of the thermal response profiles 620, 630 of RDX and PETN shown in FIG. 8A include a slow rise followed by a rapid rise to a distinct double peak, and then a fast fall. The initial slow rise can be attributed to the evaporation of nucleated islands of explosives, as discussed above. However, for the PETN and RDX response curves 620, 630, a rapid rise to a peak follows the slow rise at the melting point for each explosive. This peak may be due to the absorption of thermal energy needed to melt the PETN and RDX. The fall to the second peak followed by the fast fall is believe to be related to the exothermic decomposition of the explosives coupled with a decrease in the thermal mass, as is the case for TNT.

Figure 9A:
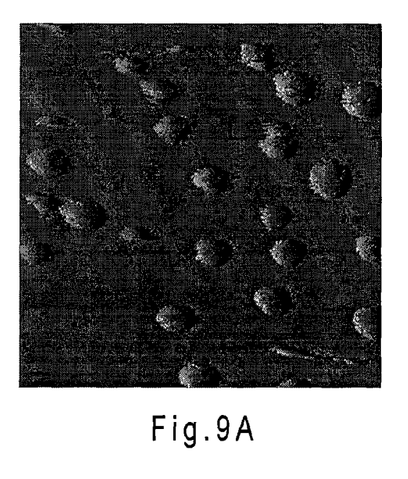
FIGS. 9A-9D are atomic force microscope (AFM) images of adsorbed analytes, including TNT (FIG. 9A), PETN (FIG. 9B), RDX (FIG. 9C), and $NH_4Cl$ (FIG. 9D), on silicon oxide surfaces.
Figure 9B:
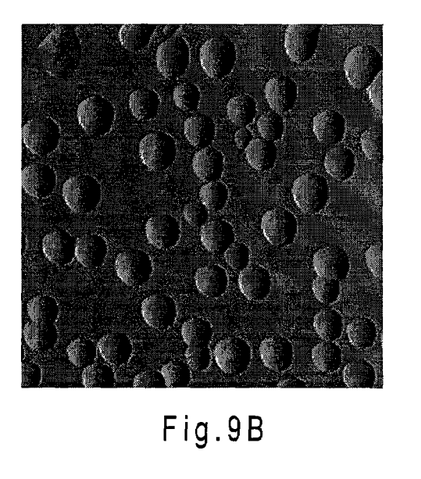
Figure 9C:
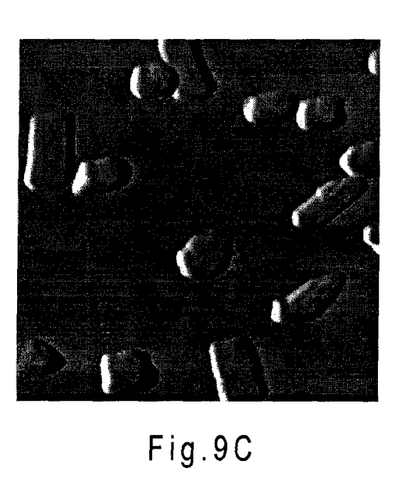
Figure 9D:
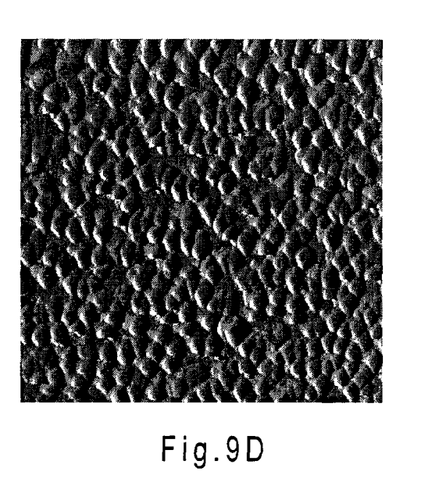

The temperatures at which the response peaks or features occur are different for different explosives, and the overshooting in the response profiles as shown in FIG. 8B is observed only for explosives. A combination of characteristic shapes and overshooting due to an exothermic process can serve as a clear indicator of a particular explosive analyte. In contrast, non-explosive analytes have thermal profiles of relatively simple shapes that indicate a pure evaporation from a uniform layer of adsorbed material. Referring to FIG. 9D, the AFM image of $NH_4Cl$ adsorbed on a silicon oxide surface of 10 square microns in area shows uniform coverage with a finite surface roughness, in contrast to the explosives imaged in FIGS. 9A-9C. The height scale of the AFM figures is 10 nm from dark to light. Mass loss due to evaporation from a uniform surface coverage is expected to be a sigmoid and the rate of evaporation is expected to follow a Gaussian profile, as observed in FIG. 7.

To illustrate high specificity in detection, sensing experiments have been conducted with interferents such as non-explosives, as discussed above, volatile organic compounds (VOCs), and water vapor. Experiments conducted with VOCs did not produce any discernable signals. One possible explanation is that the amount of mass adsorbed is less than the detection threshold. Since the VOCs have smaller sticking coefficients than the explosives, the mass loading of adsorbed VOCs on the microbridge sensor is expected to be lower.

To determine the effect of relative humidity (water vapor) on sensor performance, experiments were carried out at different humidity levels. Since the explosive vapor concentration may be millions of times smaller than the water vapor concentration in air, relative humidity may be a significant interferent to chemical vapor detection. Even at 80% relative humidity, which was the highest humidity level tested, adsorbed water molecules did not produce a thermal response signal. The results indicate that the microbridge sensor can function even in the presence of high humidity.

Figure 10:
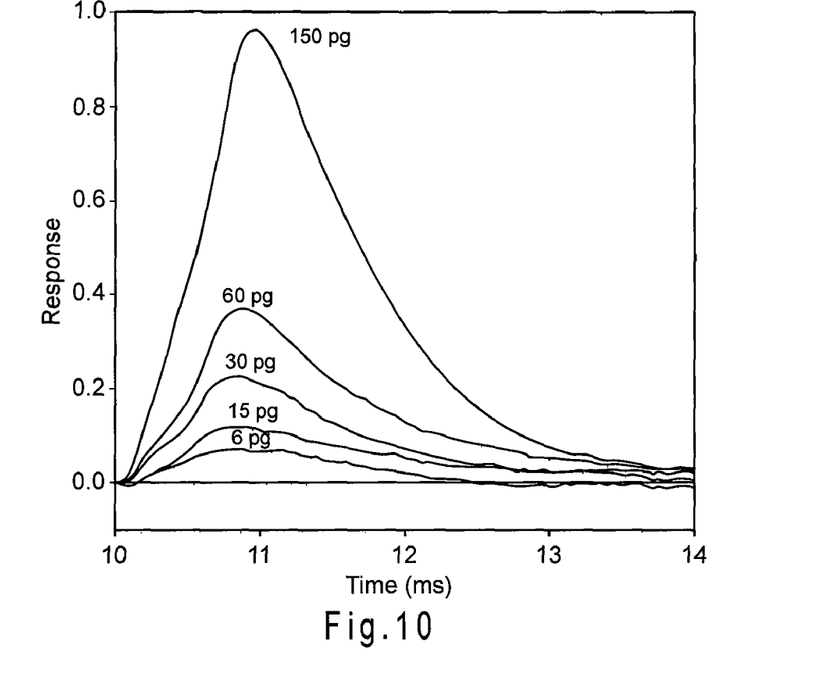
FIG. 10 shows the thermal response profiles for rapid pulsed heating of TNT at different adsorbed mass levels.

The characteristic shapes of the nanothermal profiles may be significantly influenced by the value of dT/dt. At higher dT/dt values, the observed peaks or features merge into a single peak, losing their speciation characteristics. FIG. 10 shows the nanothermal profiles obtained from a microbridge loaded with TNT when rapidly heated to 8 volts by a 20 millisecond square wave pulse. The responses for adsorbed TNT do not show any features as observed with ramped heating. Similar unresolved response profiles were obtained for fast heating of other explosives. FIG. 10 shows that under rapid heating, the peak temperature does not shift with the amount of explosive adsorbed. This is consistent with the evaporation rate of individual islands. The nonspecific response observed for explosives under rapid heating has a limit of detection (LOD) of 6 picograms, which is sufficient to detect even RDX at room temperature within 10 seconds of sampling time without the use of a preconcentrator. It is possible to combine pulsed and ramped heating approaches in such a way that ramped heating is initiated for speciation only if pulsed heating shows a response. A combined approach may yield a selective sensor for the detection and identification of explosives that is rapid, sensitive, and completely reversible. Additionally, by varying the voltage versus time function, different regimes can be highlighted. A slow increase in voltage emphasizes the evaporative regime. A rapidly increasing voltage generally leads to deflagration prior to complete sublimation. A pulsed current gives an integrated response that is indicative of the analyte formation enthalpy. It is contemplated that the microbridge sensor could be heated with a gradient as high as a few million degrees per second. An intermediate time scale (e.g., based on a voltage ramp) displays the whole range of phenomena.

The mass of adsorbed explosive vapor can be calculated using a resonating microcantilever beam placed in the same plane as the bridge sensor. For a cantilever free at one end, the frequency decreases as the adsorbed mass increases according to the relation $\Delta m/m = -2\Delta f/f$, where m and f represent the mass and resonant frequency of the cantilever, respectively. For the present bridge structure, the relationship is further complicated by the fact that both ends of the bridge are attached to the supporting substrate, and thus the surface stress resulting from the adsorption of mass alters the spring constant of the device. This makes it difficult to separate changes in resonant frequency due to mass loading (decreasing f) from changes due to surface stress (increasing f). The resonance frequency of the bridge structure can be measured by using an optical beam deflection method, which shows frequency increasing as a function of vapor adsorption due to adsorption-induced surface stress effects. Therefore, the mass of explosive vapor adsorbed on the structure may be estimated using a resonating reference cantilever device after exposure to the same duration of analyte vapor as used for the bridge device. For calibration purposes, the mass adsorption can be assumed to be uniform across the cantilever and the effective mass/area may be calculated. It also can be assumed that the mass/area is the same for the bridge sensor, and therefore the mass adsorbed on the bridge can be calculated as the product of the cantilever adsorbed mass/area with the area of the bridge surface.

From the resonance frequency measurements, the calculated limit of detection (LOD) for the fabricated microbridge device shown in FIG. 2 is estimated as approximately $0.6 \times 10^{-9}$ g (600 picograms) of adsorbed mass, which is slightly less than 1% of the inertial mass of the bridge and corresponds to about $10^{11}$ molecules. Since the vapor pressures of explosives are typically extremely small (e.g., the vapor pressure of PETN is around 5 parts-per-trillion (volume) at room temperature), a preconcentrator may be advantageous for collecting explosive molecules on the bridge surface. Preconcentrators sample large volumes of air to collect explosive molecules and/or other particulates. The collected molecules are then abruptly desorbed, at which time the explosive concentrations may be at ppb levels or higher for detection. High efficiency preconcentrators may be able to collect and concentrate low vapor pressure explosives. Exemplary preconcentrators are discussed in "Miniaturized explosives preconcentrators for use in man-portable explosives detection systems," by D. W. Hannum et al., in the *Proceedings of the IEEE* 34*th Annual* 2000 *International Carnahan Conference on Security Technology*, pp. 222-227, which is hereby incorporated by reference in its entirety. Explosives such as TNT have a relatively high vapor pressure in the parts-per-billion range, and thus may benefit from a mild preconcentration.

The ramped heating method can provide clear thermodynamic signatures which vary significantly with analyte and are therefore useful for analyte identification, even without further interpretation of the thermodynamic information contained in the response curves. However, a virtue of the method with regard to signaling the presence of energetic molecules is that it is sensitive to molecular energies. An understanding of the response in terms of thermodynamics may lead to general identification of energetic materials, even those whose signals have not been previously catalogued. Furthermore, a thermodynamic understanding may guide the design of the bridge sensors to optimize selectivity. Without wishing to be bound by theory, the following thermodynamic analysis of the microbridge sensor is set forth.

The unloaded bridge can be modeled by a total heat capacity, C (J/K), an electrical conductivity G (J/sN$^2$) and an average "cooling/heating" coefficient, k (J/K/s). The unloaded bridge temperature is well described by the simple linear differential equation:

$$C\frac{d\overline{T}}{dt} = G(V(t))^2 - k(\overline{T} - T_a) \tag{1}$$

where $T_a$ is the ambient temperature (324K) and $\overline{T}$ is the average temperature of the bridge. When the voltage is linear in time, i.e. V(t)=rt, the exact solution is:

$$\overline{T} - T_a = a\left[\left(\frac{t}{\tau}\right)^2 - 2\left(\frac{t}{\tau}\right) + 2\left(1 - \exp\left(-\left(\frac{t}{\tau}\right)\right)\right)\right] \tag{2}$$

where $\tau = C/k$ and $a = \frac{r^2 G}{k}\tau^2.$

The linearity of Eq. (1) and the linearity of the thermistor justify the assumption that the thermistor temperature, $T_T$, and the analyte temperature, $T_A$, are proportional to the average bridge temperature:

$$T_T = \frac{a_T}{a}\overline{T} \text{ and } T_A = \frac{a_A}{a}\overline{T}.$$

Hence Eq. (2) also applies to the thermistor temperature, $T_T$, or the average temperature of the analyte, $T_A$. The function $\overline{T}(t)$ is simply multiplied by $$\frac{a_T}{a} \text{ or } \frac{a_A}{a}$$

to obtain $T_T$ and $T_A$ respectively. Fitting the two constants, $\alpha_T$ and $\tau$ to the $T_T(t)$ of the unloaded bridge gives $\alpha_T$=1.7K and $\tau$=2.6 ms. Note that the time constant, $\tau$, of the bridge is a robust quantity that describes the exponential decay of temperature excursions ($\overline{T}$, $T_T$, or $T_A$) back to the ambient temperature.

Next, consider adsorbed analyte droplets on the bridge within a temperature range where the only transformation is to the vapor (evaporation or sublimation). The term vaporization is used to indicate either sublimation or evaporation. Eq. (1) is modified by the cooling due to the loss of analyte mass to vapor:

$$C\frac{d\overline{T}}{dt} = G(V(t))^2 - k(\overline{T} - T_a) + \varepsilon_V \frac{dm}{dt} \tag{3}$$

where, $\varepsilon_V$ is the enthalpy of vaporization. Taking the difference between Eqs. (1) and (3) gives:

$$C\frac{d\overline{T}_{m_0} - \overline{T}_0}{dt} = -k(\overline{T}_{m_0} - \overline{T}_0) + \varepsilon_V \frac{dm}{dt} \tag{4}$$

$$C\frac{d\Delta T}{dt} = -k(m)\Delta T + \varepsilon_V \frac{dm}{dt}$$

In Eq. (4) a cancellation of terms is achieved between the loaded and unloaded bridge that is similar to the cancellation occurring in the experiment. In Eq. (4), the heat flow that is controlled by k now returns $\Delta_T$ to zero. By comparing the solution of Eq. (4) to the measurements, it is found that more realistic values are obtained by assuming that the coating of analyte on the surface reduces the coefficient k. We postulate that the dependence of k on the load is:

$$k(m) = k(m=0)(1 - \alpha m^{2/3}) \tag{5}$$

where k(m=0) is the value determined from the unloaded bridge. The process is assumed to be activated with an activation energy $\varepsilon_A$ and to have a vaporization rate proportional to the radius of the droplet:

$$\frac{dm}{dt} = -\gamma_{T_a} \exp\left(\frac{-\varepsilon_A}{k_B T_A(t)}\right) m^{\frac{1}{3}} \tag{6}$$

The temperature controlling the activation is not $\Delta T$ but the temperature of the analyte, $T_0 + \Delta T$. The sublimation (evaporation) enthalpies for TNT, RDX, and PETN are 498 J/g (402 J/g), 588 J/g (424 J/g), and 476 J/g (422 J/g) respectively. These enthalpies set the prefactor of the vaporized mass term in Eq. (4). The prefactor, $\gamma_{T_a}$, and activation energy, $\varepsilon_A$, are not readily available but can be selected to give reasonable agreement with the evolution of the response curves below the melting points of RDX and PETN. For TNT, there is no indication of melting, and thus it is assumed that the TNT is liquid or glass through the entire measurement. The response of TNT therefore illustrates the behavior of the bridge subject to vaporization only. There is a transient stage lasting 4 ms during which evaporative cooling is either suppressed by surface contamination or is counter balanced by weak exothermic reactions related to annihilation of defects. This is followed by a period of linearly increasing $\Delta T$ as the explosive evaporates at the rate appropriate to the ambient temperature. As $\Delta T$ grows, heat flow controlled by k contributes a quadratic term that reduces $\Delta T$ from linear growth. This is balanced by increasing activation of the vaporization process, which is controlled by the temperature of the bridge. The temperature initially grows slowly, but then accelerates. Eventually, the accelerating rate of evaporation causes $\Delta T$ to increase exponentially. The rapidly increasing vaporization results in a sudden depletion of the analyte. The peak in $\Delta T$ occurs when the cooling rate due to the vaporization of a small amount of remaining analyte matches the heat flowing in. Soon afterwards the analyte is essentially gone, and, according to Eq. (4), the temperature should increase back to $T_0$ with time constant, $\tau$.

Figure 11:
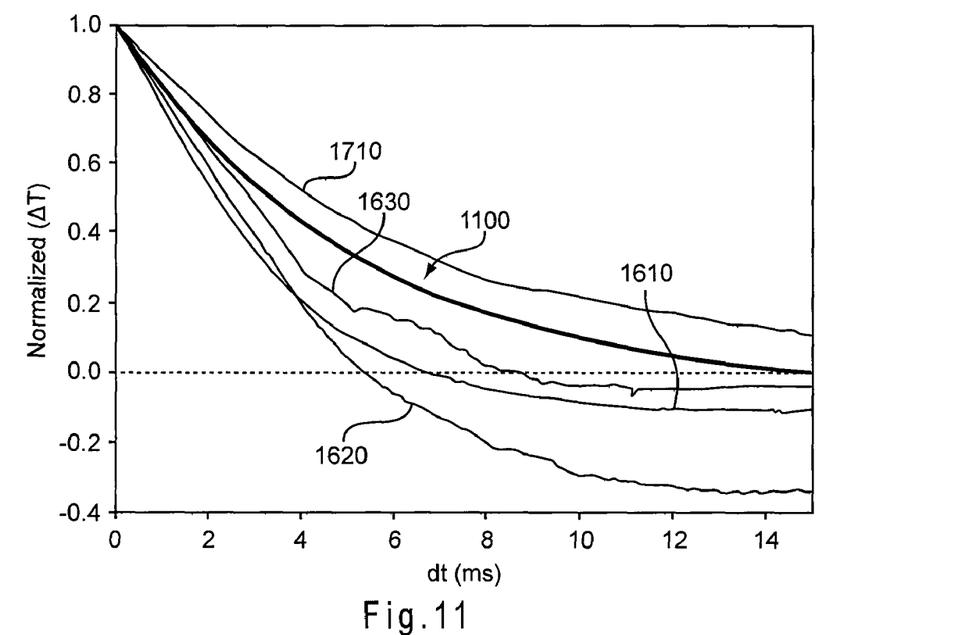
FIG. 11 is a comparison of the temperature decay rates of several analytes in comparison with the characteristic decay, which is the expected temperature return rate for a microbridge with no adsorbed analyte.

Actually, for TNT in the last stage, the observed behavior deviates from Eq. (4); the temperature increases faster than indicated by $\tau$. This may be attributed to an exothermic transformation turning on as $k_B T$ becomes comparable to the activation energy for deflagration (621 J/g). The enthalpy of deflagration (4560 J/g) is much higher than both the vaporization and melting enthalpies; therefore, even a small amount of deflagration can cause a return of $\Delta T$ to zero at a faster rate than the natural decay rate of the bridge. In fact, decay of $\Delta T$ faster or slower than indicated by the characteristic temperature decay time, $\tau$, unambiguously indicates exothermic or endothermic reactions (reverse if $\Delta T$ is negative). This is illustrated in FIG. 11, where responses are aligned in time and normalized to facilitate comparison to the characteristic decay. The characteristic decay (curve 1100) is the expected temperature return rate for a bridge with no load. The non-explosive $NH_4Cl$ (curve 1710) has a rate slower than the characteristic decay due to thermal loading, while the explosives TNT (curve 1610), PETN (curve 1620), and RDX (curve 1630) all show return rates faster than the characteristic decay due to added heat from exothermal deflagration.

In RDX, PETN, and $NH_4Cl$ melting occurs. Melting results in a cooling of the sample proportional to the enthalpy of fusion that can be appended to Eq. (4)

$$C\frac{d\Delta T}{dt} = -k\Delta T - \varepsilon_V \frac{dm}{dt} - \varepsilon_F \frac{dm_{liquid}}{dt} \quad (7)$$

Melting is assumed to take place instantaneously as a region of the analyte reaches the analyte melting point. Melting is initiated when the hottest part of the load reaches the melting point and continues until the coolest part of the load has reached the melting point. This occurs over a fairly short period of time. Therefore, the jump in $\Delta T$ due to melting can be estimated by: $\Delta T_{Melting} = \varepsilon_F m/C$.

Another feature of the data is a noticeable shift in the response as the load is increased. For larger loads, additional time (delay time) is required for the electric current to add the amount of Joule heat needed to overcome the cooling effect of vaporization and melting. The increase in heat capacity due to the specific heat of the load is found to have a very small effect on the delay. For explosives, the major contributor to the delay is the vaporization cooling. This energy loss to vaporization cooling is approximately equal to $C\Delta T$ and the delay $\Delta t_v$ is given by this energy divided by the rate at which energy is accumulating in the bridge from Joule heating:

$$\Delta t_V = C\Delta T \left(\frac{dCT_0}{dt}\right)^{-1} = \Delta T \left(\frac{dT_0}{dt}\right)^{-1} \quad (8)$$

The time delay due to melting can be estimated in a similar way:

$$\Delta t_{Melting} = \varepsilon_V m_{liquid} \left(\frac{dT_0}{dt}\right)^{-1} \quad (9)$$

For the explosives, the vaporization time delay is larger than the melting delay. For the $NH_4Cl$, the melting delay is larger. Adjusting the response curves to take these delays into effect gives alignment of response features corresponding to different loadings.

The simple analysis presented here allows thermodynamic quantities such as activation energies, enthalpies of fusion and evaporation, melting points and deflagration to be identified in the response curves. Further pursuit of this approach may yield general guidelines for the detection of energetic molecules. The range of analyte interactions affects the thermodynamic properties as a function of analyte depth because the binding of the top layer is different from that in deeper levels closer to the bridge surface. Subtle effects of this type may reveal themselves with more detailed modeling.

Although the microbridge sensor is believed to be particularly advantageous for the identification and speciation of explosive materials, its usage is not limited to explosive detection. The technique could be employed for the detection of other chemical analytes, such as those with high vapor pressures. For example, the sensor bridges could be cooled to below ambient temperature to enable enhanced adsorption or condensation of high vapor pressure analytes from the vapor phase. Carrying out the temperature cycling in an inert atmosphere may enable the investigation of the oxidative stability of analytes. The technique may also have applications in the pharmaceutical and polymer industries for investigating the temperature-dependent properties of sub-nanogram quantities of polymers and for evaluating the purity of drugs.

The demonstrated sensitivity and selectivity of this approach offer new possibilities for a single sensor-based technique that does not use a chemoselective layer for sensing. This method may also provide a technique for investigating thermally-induced properties of a wide range of materials far beyond what is possible by conventional techniques. A key advantage is that the detection process can be repeated continuously with the sensor regenerating to a pristine surface after each thermal cycle without resorting to chemical cleaning techniques. The microbridge devices described herein may provide thermal response data from sub-nanogram levels of adsorbates in a rapid, simple, and low-cost manner.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. A sensor for detecting and differentiating chemical analytes, the sensor comprising:
   a microscale body having a first end and a second end and a surface therebetween for adsorbing a chemical analyte, the surface including at least one conductive heating track for heating the chemical analyte and a conductive response track electrically isolated from the heating track for producing a thermal response signal from the chemical analyte, the heating track being electrically connected with a voltage source and the response track being electrically connected with a signal recorder, wherein the microscale body is restrained at the first end and the second end and is substantially isolated from its surroundings therebetween, the sensor thereby having a bridge configuration.

2. The sensor of claim 1 wherein the microscale body has a thickness of from about 50 nm to about 500 nm.

3. The sensor of claim 1 wherein the surface for adsorbing the chemical analyte spans an area of from about 0.01 mm² to about 0.1 mm².

4. The sensor of claim 1 wherein each of the heating track and the response track extends from the first end to the second end of the microscale body.

5. The sensor of claim 4 wherein the microscale body includes two conductive heating tracks disposed on either side of the conductive response track.

6. The sensor of claim 1 wherein the conductive heating and response tracks are embedded in the surface.

7. The sensor of claim 1 wherein the conductive heating and response tracks are electrically isolated from each other by silicon nitride.

8. The sensor of claim 1 wherein the conductive heating and response tracks comprise doped silicon.

9. The sensor of claim 1 wherein the response track is electrically connected to a Wheatstone bridge circuit including as a variable resistor an unloaded microscale body free of adsorbed chemical analyte, the Wheatstone bridge circuit providing a differential output signal to the signal recorder.

10. The sensor of claim 1 wherein the chemical analyte is an explosive.

11. The sensor of claim 10 wherein the explosive is selected from the group consisting of TNT, PETN, and RDX.

12. A method of detecting and differentiating chemical analytes, the method comprising:
providing a microscale body having a first end and a second end and a surface therebetween, the surface including at least one conductive heating track and a conductive response track electrically isolated from the heating track, wherein the microscale body is restrained at the first end and the second end and is substantially isolated from its surroundings therebetween, the sensor thereby having a bridge configuration;
adsorbing a chemical analyte onto the surface of the microscale body;
applying an increasing voltage to the heating track to heat the microscale body at a rate dT/dt for a time duration sufficient to remove substantially all of the chemical analyte from the surface;
measuring a resistance of the response track during the application of the increasing voltage over at least a portion of the time duration of the heating to generate a plurality of thermal response signals; and
recording the plurality of thermal response signals to obtain a first thermal response profile.

13. The method of claim 12 wherein the rate dT/dt is about $10^{4}$° C./s.

14. The method of claim 12 wherein the chemical analyte is heated to a temperature of at least about 500° C. over the time duration of the heating.

15. The method of claim 12 wherein the time duration of the heating is from about 10 ms to about 100 ms.

16. The method of claim 12 wherein from about 100 picograms to about 600 picograms of the chemical analyte are adsorbed onto the surface of the microscale body.

17. The method of claim 12 further comprising collecting and concentrating the chemical analyte prior to the adsorption using a preconcentrator.

18. The method of claim 12 wherein applying the increasing voltage comprises linearly ramping the voltage.

19. The method of claim 12 wherein measuring a resistance of the response track comprises employing a Wheatstone bridge circuit to make a differential measurement of the thermal response signal.

20. The method of claim 12 wherein the increasing voltage is applied to the heating track a second time after removing substantially all of the chemical analyte from the surface to obtain a second thermal response profile, the second thermal response profile being substracted from the first thermal response profile to obtain a thermal response profile of the chemical analyte.

* * * * *